US006271187B1

(12) United States Patent
Hodge et al.

(10) Patent No.: US 6,271,187 B1
(45) Date of Patent: Aug. 7, 2001

(54) HAND SOAP CONCENTRATE, USE SOLUTION AND METHOD FOR MODIFYING A HAND SOAP CONCENTRATE

(75) Inventors: Charles A. Hodge, Cottage Grove; Christopher J. Uecker, Minneapolis, both of MN (US)

(73) Assignee: Ecolab Inc., St. Paul, MN (US)

( * ) Notice: Subject to any disclaimer, the term of this patent is extended or adjusted under 35 U.S.C. 154(b) by 0 days.

(21) Appl. No.: 09/453,362

(22) Filed: Dec. 1, 1999

(51) Int. Cl.$^7$ .............................. A61K 7/00

(52) U.S. Cl. .............................. 510/130; 510/159; 510/137; 510/424; 510/426; 510/470

(58) Field of Search .............................. 510/130, 137, 510/159, 424, 426, 470

(56) References Cited

U.S. PATENT DOCUMENTS

| | | | | |
|---|---|---|---|---|
| 5,057,246 | | 10/1991 | Bertho et al. . | |
| 5,607,980 | * | 3/1997 | McAtee et al. | 514/476 |
| 5,690,920 | * | 11/1997 | Dubief | 424/70 |
| 5,816,446 | | 10/1998 | Steindorf et al. . | |
| 5,922,664 | | 7/1999 | Cao et al. . | |
| 5,922,667 | | 7/1999 | van Baggem et al. . | |
| 6,046,145 | * | 4/2000 | Santora et al. | 510/121 |

FOREIGN PATENT DOCUMENTS

| | | |
|---|---|---|
| 0 133 345 A1 | 2/1985 | (EP) . |
| 0 314 232 A2 | 5/1989 | (EP) . |
| 0 453 238 A1 | 10/1991 | (EP) . |
| WO 93/03129 | 2/1993 | (WO) . |
| WO 94/16680 | 8/1994 | (WO) . |

OTHER PUBLICATIONS

Glucopan Surfactants, Henek Corporation, CD Division, pp. 21 pages, ©, Henkel Corporation, 1992.

Hart, J. R. et al., "The Effect of Conditioning Ingredients on Lathering," *Cosmetics & Toiletries*, vol. 98, pp. 49–55 (Feb. 1983).

Woods, W.B., et al., "Nuosept C Preservative for Cosmetic and Toiletry Preparations," Nuodex Inc., Piscataway, New Jersey, reprinted from *Cosmetics and Toiletries*, vol. 100, No. 10, 4 pages (Oct. 1995).

Zonyl® Sample Kit, DuPont Performance Chemicals, Technical Information, 4 pages (Feb. 1998).

"The HLB System a time–saving guide to emulsifier selection", *ICI Americas Inc.*, 21 pages (1984).

* cited by examiner

*Primary Examiner*—Necholus Ogden
(74) *Attorney, Agent, or Firm*—Merchant & Gould P.C.

(57) ABSTRACT

A hand soap concentrate and a hand soap use solution are provided. The hand soap concentrate is provided with a viscosity of less than about 200 cps. The hand soap concentrate can be mixed with an aqueous solution to provide a use solution having a viscosity of greater than about 1,000 cps. A method for modifying a hand soap concentrate to provide a higher viscosity hand soap use solution is provided. The hand soap concentrate includes a surfactant component for removal of soil, and a component for increasing viscosity with mixing with an aqueous solution.

29 Claims, 1 Drawing Sheet

HAND SOAP CONCENTRATE, USE SOLUTION AND METHOD FOR MODIFYING A HAND SOAP CONCENTRATE

FIELD OF THE INVENTION

The invention relates to a hand soap concentrate, a hand soap use solution, and a method for modifying a hand soap concentrate to provide a higher viscosity hand soap use solution.

BACKGROUND OF THE INVENTION

Transportation costs associated with an aqueous diluent portion of a formulated aqueous product can be a significant part of the cost of aqueous liquid products. Products, such as sanitizing or cleaning solutions, when used in large amounts can be expensive to use due to transportation costs associated with the aqueous portion. For this reason, many commodity liquid products are shipped from the manufacturer as an aqueous concentrate, an aqueous alcoholic concentrate, or as a viscous concentrate to be diluted in a dispenser with an aqueous diluent at the use locus or site. For example, liquid detergents and cleaning solutions used in hospitality locations, institutional or industrial installations such as hotels, hospitals, restaurants, and the like are often shipped as liquid concentrates that are mixed and diluted using a dispensing device at an appropriate ratio to obtain a useful solution.

Concentrates can be diluted in many ways, varying from manually measuring and mixing to utilizing a computer-controlled dilution device. One common dilution technique involves utilizing a dispensing device that combines, under mixing conditions, a flow of concentrate and a flow of diluent. The flow of the liquid diluent can be directed through an aspirator such that, as the diluent passes through the aspirator, a negative pressure arises inside the aspirator drawing the liquid concentrate into the aspirator to mix with the liquid diluent. Both U.S. Pat. No. 5,033,649 to Copeland, et al. and U.S. Pat. No. 4,817,825 to Freese disclose dispensers having aspirators for diluting liquid concentrates to produce liquid products in this general way. Such aspirator-type dispensers have been used for diluting a liquid concentrate of an arbitrary viscosity with a low viscosity liquid diluent to produce a use solution of intermediate or low viscosity, i.e., the viscosity of the product falls between the viscosity of the concentrate and the diluent.

A use solution of high viscosity is often desirable. Increased viscosity can increase clinging ability to surfaces of an inclined or vertical substrate for more effective and prolonged contact. In addition, a high viscosity hand soap is often easier to use and tends to feel better than low viscosity hand soaps. Relatively viscous use solution made by diluting a low viscosity liquid concentrate with water to form a high viscosity dilute product are described in the prior art. For example, see European Publication No. 0 314 232; U.S. Pat. Nos. 5,057,246 to Bertho et al.; U.S. Pat. No. 5,922,667 to van Baggem et al.; and U.S. Pat. No. 5,922,664 to Lao et al.

A dispenser for dispensing a viscous use solution by diluting a less viscous concentrate is described in U.S. Pat. No. 5,816,446 to Steindorf, et al. which is assigned to Ecolab Inc. of Saint Paul, Minn., the assignee of this application.

SUMMARY OF THE INVENTION

Figure 1:
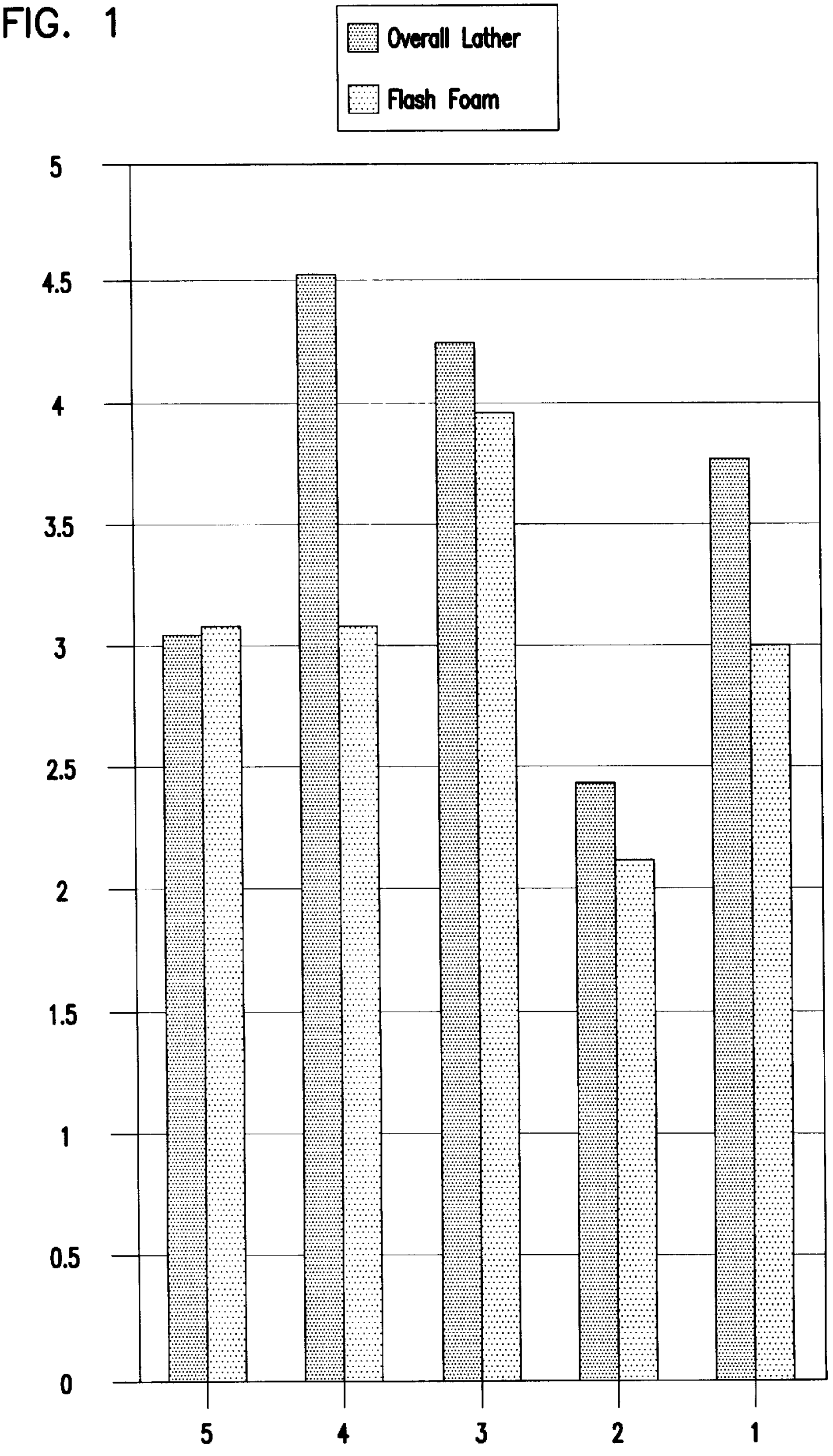
FIG. 1 is a graphical representation of data from Example 3.

A hand soap concentrate and a hand soap use solution are provided by the invention. The hand soap concentrate has a viscosity of less than about 200 cps, and can be combined with a diluent to provide a use solution having a viscosity of greater than 1,000 cps. The viscosity is preferably determined using a Brookfield viscometer. The diluent is preferably water. By diluting the liquid concentrate, a use solution having desired properties of hand feel and lather can be provided.

The concentrate includes a surfactant component for removing soil, and another component for increasing the viscosity upon dilution with a diluent, such as, water. The surfactant component preferably includes a mixture of anionic surfactant, nonionic surfactant, and amphoteric surfactant. Preferred anionic surfactants include alkyl sulfates, alkyl sulfonates, alkyl ether sulfates, alkyl ether sulfonates, alkyl aryl sulfates, alkyl aryl sulfonates, aryl sulfates, aryl sulfonates, sulfated fatty acid esters, and mixtures thereof. Preferred nonionic surfactants include alkyl polyglucoside surfactants having an HLB value of between about 10 and about 14. Preferably, the alkyl polyglucoside surfactant has an alkyl group of between about 8 and about 16 carbon atoms and a degree of polymerization of between about 0 and about 4. A preferred amphoteric surfactant includes cocamidopropyl betain.

Additional components of the hand soap concentrate preferably include thickener, salt, viscosity builder, humectant and water. Preferred thickeners include polyalkylene ether diesters. A preferred polyalkylene ether diester includes polyethylene glycol diester wherein the polyethylene glycol has between about 100 and about 200 ethylene glycol repeating units per molecule and the ester is a $C_{12}$ to $C_{18}$ ester. Preferred salts include at least one of sodium chloride, potassium chloride, sodium sulfate and potassium sulfate. Preferred viscosity builders include alkanolamide derived from a fatty acid, such as, coco-diethanolamide. Preferred humectants include at least one of propylene glycol and glycerol.

A preferred hand soap concentrate includes an anionic surfactant, an alkyl polyglucoside having an HLB value of between about 10 and about 14, a polyethylene glycol distearate having a weight average molecular weight of between about 4,000 and about 8,000, and water in an amount sufficient to provide the hand soap concentrate with a viscosity of less than about 200 cps. The alkyl polyglucoside and polyethylene glycol distearate are preferably provided at a weight ratio of alkyl polyglucoside to polyethylene glycol distearate of between about 3:1 and about 4:1.

A method for modifying a hand soap concentrate to provide a higher viscosity use solution is provided by the invention. The concentrate is provided having a viscosity of less than about 200 cps, and is mixed with water to provide a use solution having a viscosity of greater than about 1,000 cps. It should be appreciated that the water component can be provided as an aqueous solution.

It should be appreciated that the hand soap concentrates and use solutions can be characterized as detergent or soap concentrates and use solutions, and can be used in applications in addition to cleaning hands including hair cleaning (shampoos) and general skin cleaning (body wash).

DETAILED DESCRIPTION OF THE INVENTION

A hand soap concentrate according to the invention can be provided as a concentrate and processed to provide a use solution having an increased viscosity relative to the viscosity of the concentrate. In general, the concentrate should have a viscosity which allows it to be processed by the dispenser described in U.S. Pat. No. 5,816,446 to Steindorf, et al., the entire disclosure of which is incorporated herein by reference. It is generally desirable to provide the concentrate with a viscosity which allows an aspirator to move it. Preferably, the viscosity of the concentrate is less than about 200 cps. The viscosity of the use solution should be sufficiently high to provide a desirable thick and rich feel. In general, this corresponds to a use solution viscosity of greater than about 1,000 cps and more preferably greater than about 5,000 cps. The reported values of viscosity can be measured using a Brookfield viscometer.

The hand soap concentrate includes a surfactant component for removal of soils, and additional components which provide an increase in viscosity upon dilution with water. Preferably, the surfactant component includes anionic, nonionic and amphoteric surfactants. Preferably, the components which provide an increase in viscosity upon dilution with water include thickener, salt, viscosity builder, and humectant. Preservatives, dyes, and fragrances can be included.

Anionic surfactants can be useful for obtaining foaming and cleaning properties. Anionic surfactants usefuil in the invention include sulfates, sulfonates, and carboxylates such as alkyl carboxylate salts. Exemplary anionic surfactants include alkyl sulfates and sulfonates, alkyl ether sulfates and sulfonates, alkyl aryl sulfates and sulfonates, aryl sulfates and sulfonates, sulfated fatty acid esters, and mixtures thereof. Preferred anionic surfactants include linear alkyl sulfates and sulfonates, and alkyl aryl sulfates and sulfonates. More preferably the alkyl group in each instance has a carbon chain length ranging from about $C_{6-18}$, and the preferred aryl group is benzyl. A preferred anionic surfactant which can be incorporated into the concentrate of the invention is amnonium lauryl sulfate.

The anionic surfactant is preferably provided in the concentrate in an amount of between about 10 wt. % and about 24 wt. %, and more preferably between about 14 wt. % and about 20 wt. %. It should be appreciated that the amounts of components identified in this application are provided on a 100% active concentration unless otherwise specified. When a component is made available at an active concentration of less than 100%, the amount of the component which can be provided can be calculated based upon the amount identified at a 100% active concentration.

Nonionic surfactants can be usefuil for obtaining desirable flow and foam boost properties. Exemplary nonionic surfactants include alkyl polyglucoside surfactants. The applicants have found that alkyl polyglucoside surfactants reduce the tendency of the use solution to clump, and allows the concentrate to pour freely. Preferred alkyl polyglucoside surfactants include those having an HLB value of between about 10 and about 14. In generally, when the HLB value is too low or too high, the concentrate becomes unstable. Lack of stability can be observed by phase separation within the temperature range of 40° F. and 120° F. Preferred alkyl polyglucoside surfactants have an alkyl group of between about 8 and about 16 carbon atoms, and a degree of polymerization of between about 0 and 4 glucose units. A preferred alkyl polyglucoside is available under the name Glucopon 625 from Henkel Corporation of Ombler, Pa.

The nonionic surfactant is preferably provided in an amount which provides the concentrate with desirable flow properties and foam boost properties. In the concentrate, the amount of nonionic surfactant is preferably provided in an amount of between about 1 wt. % and about 10 wt. %, and more preferably between about 2 wt. % and about 7 wt. % based upon a 100% active solution of nonionic surfactant. Alkyl polyglucoside is commonly available at a 50% active solution. The amount of alkyl polyglucoside based upon a 50% active solution is then calculated.

A thickener is provided which will increase the viscosity of the use solution upon dilution in water. The thickener provides the use solution with desirable after-feel properties. Preferred thickeners include polyalkylene ether diesters. The polyalkylene ether component is preferably polyethylene glycol having ethylene glycol repeating units of between about 100 and about 200, and more preferably between about 130 and 170. The ester components are preferably $C_{12}$ to $C_{18}$ diesters including dilaurate and distearate. Preferred thickeners include polyethylene glycol distearate and polyethylene glycol dilaurate. In general, the molecular weight of the thickener should not be so high that the thickener is insoluble in the concentrate, and should not be so low that the thickener does not build up sufficient viscosity in the use solution. Preferably, the thickener exhibits a weight average molecular weight of between about 4,000 and about 8,000. A preferred thickener is commonly referred to as PEG 150 distearate and has a weight average molecular weight of about 6,000. A commercial form of PEG 150 distearate is available under the name Calgene 602-S from Lambert Technologies.

The thickener is preferably provided in the concentrate in an amount of between about 0.25 wt. % and about 5.0 wt. %. Preferably, the thickener is provided in the concentrate in an amount of between about 0.5 wt. % and about 2.0 wt. %.

The ratio of nonionic surfactant to thickener is preferably provided so that the concentrate exhibits a viscosity of less than about 200 cps and the use solution exhibits a viscosity of greater than about 1,000 cps. Preferably, the ratio of nonionic surfactant (alkyl polyglucoside) to thickener (polyethylene glycol distearate) is between about 3:1 and about 4:1.

The concentrate preferably includes water in an amount sufficient to keep the concentrate in solution and maintain the viscosity of the concentrate at or below 200 cps. Increasing the concentration of water above about 60 wt. % tends to thicken the concentrate, and providing less than about 35 wt. % water results in a concentrate which may become unstable. Preferably, the amount of water provided in the concentrate is between about 40 wt. % and about 52 wt. %. It is expected that much of the water will be provided as a result of its presence in combination with other components which are used to generate the soap concentrate.

A salt is included in the concentrate to provide thickening when additional water is introduced into the concentrate. Preferred salts provide a pH that remains relatively neutral. It should be understood that the phrase "relatively neutral" refers to the concentrate having a pH between about 6 and about 8. Preferred salts are those which do not shift the pH too dramatically. Exemplary salts include sodium chloride, potassium chloride, sodium sulfate, and potassium sulfate. In order to provide the use solution with a sufficiently high viscosity, the salt component is preferably provided in the concentrate in an amount of between about 1 wt. % and about 12 wt. %, and more preferably in an amount of between about 4 wt. % and about 8 wt. %.

The concentrate can include a viscosity builder which provides for thickening when the concentrate is diluted with water. Preferred viscosity builders are alkanolamides derived from fatty acids. A preferred alkanolamide is cocodiethanolamide. Preferably, the viscosity builder is provided in the concentrate in an amount of between about 6 wt. % and about 25 wt. %, and more preferably in an amount of between about 12 wt. % and about 20 wt. %.

The concentrate preferably includes an amphoteric surfactant. The amphoteric surfactant is provided for generating lather. Preferred amphoteric surfactants include betaine derivatives. A preferred betaine derivative is cocamidopropyl betaine. The amphoteric surfactant is preferably used in the concentrate in an amount of between about 1 wt. % and about 10 wt. %, and more preferably in an amount of between 2 wt. % and about 6 wt. %.

In order for the amphoteric surfactant to finction as a lathering agent, it is desirable to provide the concentrate at a relatively neutral pH. Preferably, the pH of the concentrate is between about 6 and about 8 and the pH of the use solution is below about 7. Accordingly, buffering agents can be used to provide the concentrate with a pH between about 6 and about 8 and the use solution with a pH below about 7. Preferred buffering agents include a lactic acid and citric acid. The amount of buffering agent is incorporated to provide the desired pH.

The concentrate preferably includes a humectant to reduce skin irritation. Too much humectant can cause instability in the concentrate, and too little humectant can result in a thickened concentrate which does not flow through diluting apparatus. Preferably, the humectant is provided in the concentrate in an amount of between about 2 wt. % and about 12 wt. %, and more preferably in an amount of between about 4 wt. % and about 8 wt. %. Exemplary humectants include propylene glycol, glycerol, mixtures of propylene glycol and glycerol, and humectants containing small amounts of propylene glycol and/or glycerol.

A preservative can be incorporated into the concentrate. It should be understood that the invention can be practiced without the use of a preservative. When a preservative is used, it is preferably used in an amount which provides preservative properties in the use solution. For most commercially available preservatives, the amount of preservative provided in the concentrate is between about 0 and about 4 wt. %, and more preferably between about 0.01 wt. % and about 2 wt. %. A preferred preservative is polymethoxy bicyclic oxazolidine which is available under the name Nuosept C from Costec, Inc.

Additional components which can be incorporated into the concentrate include dyes and fragrances. The dyes and fragrances which can be used in the concentrate include those dyes and fragrances which are conventionally available. Dyes which can be used according to the invention are disclosed in Colour Index: Pigments and Solvent Dyes: Third Edition, published by the Society of Dyers and Colourists in 1989. Fragrances which can be used according to the invention include those disclosed in Common Fragrances and Flavour Materials: Second Edition, by VCH Publishers, published 1990.

Provided in Table 1 is a preferred composition of the hand soap concentrate according to the invention. The composition identified in Table 1 can include a sufficient amount of a buffering agent to provide the concentrate with a pH of between about 6 and about 8. If ammonium laureth sulfate is included in the concentrate, the buffer is preferably provided in an amount to provide the concentrate with a pH of below about 7.

TABLE 1

| Component | Range | Preferred Range |
|---|---|---|
| anionic surfactant | 10 wt. % to 24 wt. % | 14 wt. % to 20 wt. % |
| nonionic surfactant | 1 wt. % to 10 wt. % | 2 wt. % to 7 wt. % |
| thickener | 0.25 wt. % to 5.0 wt. % | 0.5 wt. % to 2.0 wt. % |
| salt | 1 wt. % to 12 wt. % | 4 wt. % to 8 wt. % |
| viscosity builder | 6 wt. % to 25 wt. % | 12 wt. % to 20 wt. % |
| amphoteric surfactant | 1 wt. % to 10 wt. % | 2 wt. % to 6 wt. % |
| humectant | 2 wt. % to 12 wt. % | 4 wt. % to 8 wt. % |
| preservative | 0 to 4 wt. % | 0.01 wt. % to 2 wt. % |
| dye | 0 to 0.2 wt. % | 0.01 wt. % to 0.1 wt. % |
| fragrance | 0 to 1 wt. % | 0.01 wt. % to 0.5 wt. % |
| water | 35 wt. % to 60 wt. % | 40 wt. % to 52 wt. % |

EXAMPLE 1

This example provides a comparison of flash foam, overall lather and clumping properties of five hand soap compositions. In general, flash foam refers to the foam generated on a user's hands one or two seconds after initiating scrubbing. Overall lather refers to the foam present at the end of the hand wash. Clumping refers to the presence, in the use solution, of clumps which inhibit the free flow of the use solution.

The compositions of the five tested concentrates are provided in Table 2 where each component is identified by a weight percent. The concentrates were diluted with tap water to provide use solution containing 13 wt. % concentrate and 87 wt. % tap water.

The use solutions were evaluated by a panel of 25 individuals. Each panelist was asked to wash his or her hands with a standard hand soap to ensure a consistent soil level from panelist to panelist. Each panelist was then asked to evaluate, in a random order, each hand soap for quick foam and overall lather on a scale of one to five where one represents poor properties and five represents excellent properties. With respect to the evaluation of clumping, the higher numbers refer to a decrease in the observation of clumping. The results are reported in Table 2 as average values.

Formulation 1 is liquid concentrate hand soap from Costec, Inc. Formulation 1 provides a hand soap use solution which exhibits an undesirable degree of clumping. That is, the use solution does not flow sufficiently well over a user's hands and does not solubilize with water very easily. Formulations 2–5 were provided to improve the clumping property exhibited by the use solution generated from formulation 1. In Formulation 2, a nonionic surfactant, sorbitan monooleate, was added. In Formulation 3, the amount of anionic surfactant (ammonium laureth sulfate) was increased and the amount of thickener (polyethylene glycol distearate) was decreased. In Formulation 4, a fluorosurfactant was added. In Formulation 5, nonionic surfactant (lauryl polyglucose) was added.

TABLE 2

| | Formulation 1 | Formulation 2 | Formulation 3 | Formulation 4 | Formulation 5 |
|---|---|---|---|---|---|
| deionized water | 40.2 | 41.1 | 40.1 | 40.7 | 41 |
| sodium chloride | 8.8 | 7.9 | 7 | 8 | 7 |
| propylene glycol | 6 | 5.4 | 6 | 6 | 6 |
| ammonium laureth sulfate[1] | 18.4 | 16.6 | 23.1 | 18.4 | 17.3 |
| polyethylene glycol distearate[2] | 3.6 | 3.2 | 1.4 | 2.5 | 1.4 |
| diethanol coconut amide[3] | 16.2 | 14.6 | 16.2 | 16.2 | 16.2 |
| cocamidopropyl betaine[4] | 4.8 | 4.3 | 4.8 | 4.8 | 4.8 |
| fluorosurfactant[5] | | | | 1 | |
| lactic acid (88%)[6] | 1 | 0.5 | 0.2 | 1 | 0.2 |
| polymethoxy bicyclic oxazolidine[7] | 1 | 0.9 | 0.9 | 1 | 0.9 |
| dye | | 0.1 | 0.1 | 0.1 | 0.1 |
| sorbitan monooleate | | 4.5 | | | |
| fragrance | | 1 | 0.4 | 0.4 | 0.4 |
| laury polyglucose[8] | | | | | 4.8 |
| flash foam (average) | 1.9 | 2 | 2.9 | 1.5 | 3.2 |
| overall lather (average) | 2 | 2.4 | 3.1 | 2.1 | 3.5 |
| clumping (average) | 2.3 | 1.9 | 2.9 | 3.5 | 3.7 |

[1]Ammonium laureth sulfate is available under the name Sulfochem EA-60 from Chemron.
[2]Polyethylene glycol distearate is available under the name Calgene 602-S from Lambert Technologies.
[3]Diethanol coconut amide is available under the name Amidex CE from Chemron.
[4]Cocamidopropyl betaine is available under the name Betaine Cap B-35 from Deforest.
[5]Fluorosurfactant is available under the name Zonyl from DuPont.
[6]Lactic acid is available under the name Purac HQ-88 from Purac.
[7]Polymethoxy bicyclic oxazolidine is available under the name Nuocept C from Costec, Inc.
[8]Lauryl polyglucose is available under the name Glucopon 625 UP from Henkel.

EXAMPLE 2

This panel experiment was provided to compare the flash foam and overall lather properties of hand soaps.

A panel of 25 individuals was asked to evaluate three hand soaps for quick foam and overall lather. The first hand soap was prepared from the concentrate shown in Table 3 as Concentrate 1. The second hand soap was prepared from a concentrate identified in Table 3 as Concentrate 2. Concentrates 1 and 2 were each mixed with tap water to provide use solutions containing 13 wt. % concentrate and 87 wt. % tap water. The third hand soap was provided as a ready-to-use product having the formulation identified in Table 3. The ready-to-use product is considered a premium hand soap product.

Each panelist was first asked to wash his or her hands with a standard hand soap to ensure a consistent soil level from panelist to panelist. Each panelist was then asked to evaluate, in random order, each hand soap for flash foam and overall lather on a scale of one to five where one corresponds to poor properties and five corresponds to excellent properties. The results are reported in Table 3.

TABLE 3

| | Concentrate 1 | Concentrate 2 | Ready-To-Use Product |
|---|---|---|---|
| deionized water | 36.5 | 41 | 76.6 |
| sodium chloride | 7 | 7 | 0.5 |
| propylene glycol | 5.6 | 6 | 0.6 |
| ammonium laureth sulfate | 23.1 | 17.3 | |
| sodium lauryl ether ethoxylate | | | 1.2 |
| polyethylene glycol distearate | 2.4 | 1.4 | |
| diethanol coconut amide | 16.2 | 16.2 | |
| cocamidopropyl betaine | 4.8 | 4.8 | |
| polyethylene glycol mono laurate | 1 | | |
| lactic acid | 1 | 0.2 | |
| polymethoxy bicyclic oxazolidine | 1 | 0.9 | |
| dye | 0.1 | 0.1 | 0.1 |
| sorbitan monooleate | | | |
| fragrance | 0.4 | 0.4 | 0.2 |
| lauryl polyglucose | | 4.8 | 20.5 |
| chloro-dichlorophenoxy phenol | | | 0.6 |
| flash foam (average) | 2.4 | 2.9 | 3.2 |
| overall lather (average) | 2.9 | 3.1 | 3.8 |

EXAMPLE 3

This panel experiment was designed to evaluate the flash foam and overall lather properties of hand soap. For the purposes of this experiment, flash foam refers to the foam generated with the first scrub. Overall lather refers to the foam which is generated during the hand washing process until just prior to rinsing.

A panel of 25 individuals was used to evaluate five use solution hand soaps made up from concentrates which varied from the base concentrate formula in the levels of four materials. The raw materials that were varied for this experiment were: lauryl polyglucose, sodium chloride, lauryl amine sulfate and PEG 150 Distearate. The base concentrate is identified as Formulation 5 in Table 2.

The concentrates (1–5) in Table 3 were prepared from the base concentrate by adding lauryl polyglucose, sodium chloride, polyethylene glycol, and ammonium lauryl ether. The amount of each component added to the base concentrate is identified in Table 4. Use solutions were prepared by diluting each concentrate with water to provide a use solution containing 13 wt. % concentrate and 87 wt. % water.

TABLE 4

| Concentrate | lauryl polyglucose | sodium chloride | PEG | ammonium lauryl ether |
|---|---|---|---|---|
| 1 | 7.05 | 8 | 0.75 | 19.2 |
| 2 | 2.00 | 8 | 2.25 | 13.2 |
| 3 | 4.03 | 6 | 1.50 | 16.2 |
| 4 | 7.00 | 4 | 2.25 | 19.2 |
| 5 | 2.00 | 4 | 0.75 | 19.2 |

Each panelist was first asked to wash his or her hands with a standard hand soap to ensure a consistent soil level from panelist to panelist. Each panelist was then asked to evaluate, in a random order, each hand soap for quick foam and lather on a scale of one to five where one equals poor foam and five equals excellent foam. The results were tabulated and averaged and the standard deviation calculated. The results are provided in Table 5 and FIG. 1.

TABLE 5

| | hand soap 1 | hand soap 2 | hand soap 3 | hand soap 4 | hand soap 5 |
|---|---|---|---|---|---|
| overall lather | 3.76 | 2.44 | 4.24 | 4.52 | 3.04 |
| flash foam | 3 | 2.12 | 3.96 | 3.08 | 3.08 |

The above specification, examples and data provide a complete description of the manufacture and use of the composition of the invention. Since many embodiments of the invention can be made without departing from the spirit and scope of the invention, the invention resides in the claims hereinafter appended.

We claim:

1. A hand soap concentrate comprising:

about 14 wt. % to about 24 wt. % anionic surfactant;

about 1 wt. % to about 10 wt. % nonionic surfactant;

about 0.25 wt. % to about 5.0 wt. % thickener;

about 1 wt. % to about 12 wt. % salt;

about 6 wt. % to about 25 wt. % viscosity builder;

about 1 wt. % to about 10 wt. % amphoteric surfactant;

about 2 wt. % to about 12 wt. % humectant; and about 35 wt. % to about 60 wt. % water;

wherein the hand soap concentrate exhibits a viscosity of less than about 200 cps.

2. A hand soap concentrate according to claim 1, wherein the anionic surfactant comprises at least one of alkyl sulfates, alkyl sulfonates, alkyl ether sulfates, alkyl ether sulfonates, alkyl aryl sulfates, alkyl aryl sulfonates, aryl sulfates, aryl sulfonates, sulfated fatty acid esters, and mixtures thereof.

3. A hand soap concentrate according to claim 1, wherein the anionic surfactant is provided in an amount of between about 14 wt. % and about 20 wt. %.

4. A hand soap concentrate according to claim 1, wherein the nonionic surfactant comprises alkyl polyglucoside having an alkyl group of between about 8 and about 16 carbon atoms and a degree of polymerization of between about 0 and about 4.

5. A hand soap concentrate according to claim 1, wherein the nonionic surfactant comprises alkyl polyglucoside in an amount of between about 2 wt. % and about 7 wt. %.

6. A hand soap concentrate according to claim 1, wherein the thickener comprises a polyalkylene ether diester.

7. A hand soap concentrate according to claim 6, wherein the polyalkylene ether diester comprises a polyethylene glycol diester wherein the polyethylene glycol comprises between about 100 and about 200 ethylene glycol repeating units and the ester comprises $C_{12}$ to $C_{18}$ ester.

8. A hand soap concentrate according to claim 1, wherein the thickener comprises polyethylene glycol distearate in an amount of between about 0.5 wt. % and about 2.0 wt. %.

9. A hand soap concentrate according to claim 1, wherein the water is provided in an amount of between about 40 wt. % and about 52 wt. %.

10. A hand soap concentrate according to claim 1, wherein the humectant comprises at least one of propylene glycol and glycerol.

11. A hand soap concentrate according to claim 1, wherein the humectant is provided in an amount of between about 4 wt. % and about 8 wt. %.

12. A hand soap concentrate according to claim 1, wherein the amphoteric surfactant comprises cocamidopropyl betaine.

13. A hand soap concentrate according to claim 1, wherein the amphoteric surfactant is provided in an amount of between about 2 wt. % and about 6 wt. %.

14. A hand soap concentrate according to claim 1, wherein the viscosity builder comprises alkanolamide derived from a fatty acid.

15. A hand soap concentrate according to claim 14, wherein the alkanolamide derived from a fatty acid comprises coco-diethanolamide.

16. A hand soap concentrate according to claim 1, wherein the viscosity builder is provided in an amount of between about 12 wt. % and about 20 wt. %.

17. A hand soap concentrate according to claim 1, wherein the salt comprises at least one of sodium chloride, potassium chloride, sodium sulfate and potassium sulfate.

18. A hand soap concentrate according to claim 1, wherein the salt is provided in an amount of between about 4 wt. % and about 8 wt. %.

19. A hand soap concentrate comprising:

about 14 wt. % to about 24 wt. % anionic surfactant;

alkyl polyglucoside having an HLB value of between about 10 and about 14;

polyethylene glycol distearate having a weight average molecular weight of between about 4,000 and about 8,000;

about 35 wt. % to about 60 wt. % water to provide the hand soap concentrate with a viscosity of less than about 200 cps; and wherein the weight ratio of alkyl polyglucoside to polyethylene glycol distearate is between about 3:1 and about 4:1.

20. A hand soap concentrate according to claim 19 wherein the anionic surfactant comprises at least one of alkyl sulfates, alkyl sulfonates, alkyl ether sulfates, alkyl ether sulfonates, alkyl aryl sulfates, alkyl aryl sulfonates, aryl sulfates, aryl sulfonates, sulfated fatty acid esters, and mixtures thereof.

21. A hand soap concentrate according to claim 19, wherein the alkyl polyglucoside comprises an alkyl group of between about 8 and about 16 carbon atoms and a degree of polymerization of between about 0 and about 4.

22. A hand soap concentrate according to claim 19, further comprising a humectant selected from at least one of propylene glycol and glycerol.

23. A hand soap concentrate according to claim 17, further comprising an alkanolamide derived from a fatty acid.

24. A hand soap concentrate according to claim 19, further comprising an amphoteric surfactant.

25. A hand soap concentrate according to claim 19, further comprising a salt selected from at least one of sodium chloride, potassium chloride, sodium sulfate, and potassium sulfate.

26. A method for modifying a hand soap concentrate to provide a higher viscosity hand soap use solution, the method comprising steps of:

(a) mixing a hand soap concentrate having a viscosity of less than about 200 cps with water to provide a hand soap use solution having a viscosity of greater than about 1,000 cps, said hand soap concentrate comprising:

about 14 wt. % to about 24 wt. % anionic surfactant;

about 1 wt. % to about 10 wt. % nonionic surfactant;

about 0.25 wt. % to about 5.0 wt. % thickener, about 1 wt. % to about 12 wt. % salt;

about 6 wt. % to about 25 wt. % viscosity builder;

about 1 wt. % to about 10 wt. % amphoteric surfactant;

about 2 wt. % to about 12 wt. % humectant; and
about 35 wt. % to about 60 wt. % water.

27. A method for modifying a hand soap concentrate to provide a higher viscosity hand soap use solution, the method comprising steps of:

(a) mixing a hand soap concentrate having a viscosity of less than about 200 cps with water to provide a hand soap use solution having a viscosity of greater than about 1,000 cps, said hand soap concentrate comprising:

about 14 wt. % to about 24 wt. % anionic surfactant;
alkyl polyglucoside having a HLB value of between about 10 and about 14;

polyethylene glycol distearate having a weight average molecular weight of between about 4,000 and about 8,000;
about 35 wt. % to about 60 wt. % water; and
wherein the ratio of alkyl polyglucoside to polyether glycol distearate is between about 3:1 and about 4:1.

28. A hand soap concentrate according to claim 1, wherein the nonionic surfactant consists essentially of alkyl polyglucoside.

29. A method for modifying a hand soap concentrate according to claim 26, wherein the nonionic surfactant consists essentially of alkyl polyglucoside.

* * * * *